United States Patent [19]

Shaw

[11] Patent Number: 5,637,092

[45] Date of Patent: Jun. 10, 1997

[54] SYRINGE PLUNGER LOCKING ASSEMBLY

[76] Inventor: Thomas J. Shaw, 1510 Hillcrest, Little Elm, Denton County, Tex. 75068

[21] Appl. No.: 380,107

[22] Filed: Jan. 30, 1995

[51] Int. Cl.⁶ .............................................. A61M 5/00
[52] U.S. Cl. ................................... 604/110; 604/195
[58] Field of Search ................................ 604/181, 110, 604/195, 187, 192, 218, 222, 226

[56] References Cited

U.S. PATENT DOCUMENTS

| | | | |
|---|---|---|---|
| 4,978,339 | 12/1990 | Labouze et al. | 604/110 |
| 5,019,044 | 5/1991 | Tsao | 604/110 |
| 5,049,133 | 9/1991 | Pascual | 604/110 |
| 5,064,419 | 11/1991 | Gaarde | 604/195 |
| 5,090,962 | 2/1992 | Landry, Jr. et al. | 604/110 |
| 5,114,404 | 5/1992 | Paxton et al. | 604/110 |
| 5,152,750 | 10/1992 | Haining | 604/195 |
| 5,163,918 | 11/1992 | Righi et al. | 604/198 |
| 5,180,369 | 1/1993 | Dysarz | 604/110 |
| 5,267,961 | 12/1993 | Shaw | 604/110 |
| 5,304,138 | 4/1994 | Mercado | 604/110 |
| 5,308,331 | 5/1994 | Avila et al. | 604/110 |
| 5,370,620 | 12/1994 | Shonfeld | 604/110 |
| 5,376,080 | 12/1994 | Petrussa | 604/198 |
| 5,407,436 | 4/1995 | Toft et al. | 604/195 |
| 5,415,646 | 5/1995 | Roth | 604/110 |

Primary Examiner—Robert A. Hafer
Assistant Examiner—Ronald K. Stright, Jr.
Attorney, Agent, or Firm—Harris, Tucker & Hardin, P.C.

[57] ABSTRACT

A locking assembly for the plunger of a syringe locks the plunger head inside the body of the syringe when the plunger is depressed at the end of an injection cycle. The inner wall of the syringe body has a constriction which projects inwardly toward the center. The head of the plunger has a catch adapted to cooperate with the constriction and hook the plunger when the plunger is depressed. A flexible shield or seal member is mounted on the plunger head adjacent the catch to prevent trapping of air bubbles under the catch during movement of the plunger while the syringe is being filled with injection fluid and readied for use. The locking assembly is particularly suited for use with a retractable syringe design.

21 Claims, 4 Drawing Sheets

SYRINGE PLUNGER LOCKING ASSEMBLY

BACKGROUND OF THE INVENTION

1. Field of the Invention

This invention relates to a medical device, and more particularly, to a locking assembly for the plunger of a syringe.

2. Background of the Art

Retractable syringe technology has been a rapidly advancing art fueled by concern with the threat of the disease AIDS in the general population and the belief that a major cause of this problem is a result of the sharing and reuse of hypodermic syringes by IV drug users. An important collateral problem is the problem of accidental needle sticks among health care workers and sanitation employees of hospitals from syringe needles that had been used on infected patients.

Many of the known single use retractable syringes have mechanisms which permit retraction of the used needle into the syringe body or plunger of the syringe after use. Many of the known devices employ some kind of triggering mechanism by which the syringe needle is automatically retracted into the syringe body when the plunger is depressed at the end of an injection cycle. Exemplary of one type of such automatically retractable syringe is found in my own patent application, Ser. No. 08/125,292, now U.S. Pat. No. 5,385,551 although there are a number of other devices with at least a portion of a retraction mechanism in a front end portion of a syringe which retract automatically when the plunger is depressed to complete an injection. In a number of such cases, the hollow plunger is sealed with a plug member or a diaphragm at the front of the plunger which is dislodged, pierced or broken when the plunger is depressed to inject the last of the injection fluid from the plunger and a needle holding element is driven up into the hollow plunger so that the sharp needle is no longer exposed.

It has been found possible to employ a catch on the front of a syringe plunger which hooks a projection on the inside of the syringe body at about the time a retraction mechanism is being triggered by continued depression of the plunger after the injection is completed. It is highly desirable to prevent the plunger from being withdrawn from the syringe body after the needle is retracted so that it is very difficult for a subsequent user to take the syringe apart and reassembly the components for reuse. This is true even for syringes which do not have a retractable needle. If the plunger cannot be pulled back after one use, then it cannot be reused, although if the needle is not retracted, there remains a risk of needle sticks.

It has been found that bubbles of air tend to accumulate under any kind of catch on the front tip end of a syringe plunger during the process of filling with injection fluid a syringe having a locking plunger. Some air inevitably remains in the variable fluid chamber of the syringe when the needle is placed in a vial of fluid and the plunger is withdrawn to create a vacuum which will draw injection fluid into the injection chamber. This entrained air generally exhibits itself as bubbles which are visible through the clear walls of the typical syringe.

The usual procedure to deal with these bubbles is to hold the syringe vertical while lightly depressing the plunger to expel the undesirable air bubbles while adjusting the dose by expelling a small quantity of the injection fluid through the needle. This operation is sometimes accompanied by tapping the wall to release the bubbles which tend to adhere by surface tension, but are usually easily dislodged. However, it is found that when the tip of the syringe plunger is equipped with a catch which may be visualized in cross section as a form of arrowhead, a transverse surface is present which becomes an ideal place for these bubbles to accumulate.

It might be possible to alleviate this problem if the usual seal on the head of the plunger which is designed for sliding contact with the walls of the syringe body is abutted up against the catch on the tip of the syringe. While this has the prospect of eliminating the accumulation of bubbles under the catch, it makes it very difficult to create a locking mechanism because of interference between the seal and the cooperating portion of the locking mechanism on the syringe body. In addition, the seal may undesirably increase the amount of force required to depress the plunger in order to move it to the locking position and interfere with smooth operation of any retraction mechanism.

Consequently, there is a need for a syringe plunger locking assembly for use with a single use syringe having a syringe plunger with a catch wherein bubbles of air are prevented from accumulating behind the catch or are easily released therefrom, without interfering with the smooth depression of the plunger. Such a locking mechanism should not increase the force necessary to depress the plunger and trigger a retraction mechanism and without deteriorating the smooth operation and the extreme degree of reliability necessary in a syringe with a retraction mechanism.

SUMMARY OF THE INVENTION

The present invention is a syringe plunger locking assembly which is mainly usable in a syringe having a hollow syringe body elongated longitudinally and divided internally between a front portion and a hollow back portion wherein an exposed injection needle in the front portion extends in fluid communication with the hollow back portion of the syringe body. Such a syringe has a movable plunger having a head end disposed within the hollow syringe body, a plunger head having a sliding seal mounted thereon in sliding contact with the inner wall surface of the syringe body to define a variable chamber for injection fluid in the back portion thereof whereby injection fluid may be passed through a needle upon movement of the plunger. The improved locking assembly is especially useful in a retractable syringe having a retractable needle in a hollow front portion of the syringe body.

The improved locking assembly comprises a constriction being located on the interior wall of the syringe body between the front and back portions. The head of the plunger has a catch adapted to cooperate with the constriction and hooks the plunger when the plunger is depressed to complete an injection. A flexible shield or seal member is mounted on the plunger head adjacent the catch to prevent trapping of bubbles under the catch during movement of the plunger while the syringe is being filled with injection fluid and readied for use.

More particularly, the plunger head has a leading tip portion which carries the catch and has the ability to flex resiliently in order to aid in hooking of the plunger with the constriction. The flexible shield is carried by the plunger head over a depression behind the catch. The constriction in the syringe body preferably has a downwardly and inwardly angled surface leading to the narrowest point thereof which cooperates with a corresponding tapered outer surface on a tip portion of the plunger head to facilitate flexing of the tip portion as the plunger head passes into the constriction. The constriction may be described as being formed as an annular ramp on the inner wall surface of the syringe body culminating in an edge which engages the catch on the plunger head tip portion as soon as the catch passes therethrough in response to outward flexing of the tip portion of the plunger head.

The catch on the tip portion of the plunger head preferably comprises a plurality of resilient fingers which serve to engage the annular ramp in response to depression of the plunger at the end of an injection cycle.

The sliding seal around the head of the plunger is spaced apart from the catch behind the depression and the flexible shield is positioned between the sliding seal and the catch and over the depression at a radial distance from the center line of the plunger generally equal to the radial distance of the catch. The flexible shield can be a separate seal member radially even with the catch which is spaced above the depression or it may constitute a forward extension integral with the normally used sliding seal in the form of a thin wall radially level with the catch and spaced above the depression. In either case, the plunger has longitudinally spaced apart front and back stops and the sliding seal on the plunger is sized to fit in the space between the stops so that it is held in fixed position on the plunger and cannot move relative thereto. The depression behind the catch is formed between the front stop and the catch and the forward extension of the sliding seal passes over the front stop and above the depression to reach the catch. Since the sliding seal is radially even with the outer most extending part of the catch, there is no "ledge" available under which bubbles can accumulate and be held against their natural buoyancy when the syringe is held vertically.

Because the flexible shield or seal member is spaced over the depression behind the catch, it is free to give inwardly when the catch passes the constriction and does not affect the cooperative locking of the catch and the constriction as the tip of the plunger passes into and through the constriction.

Alternately, the seal member can be a separate soft easily compressed material, much softer than the sliding seal, which fully occupies the depression, such as an elastomeric foam or soft silicone rubber ring member suitably selected to withstand sterilization of the syringe components. The soft ring member would have to compress very easily so that the portion of an inward projection that comprises the constriction compress the ring member without interfering with the locking action.

DETAILED DESCRIPTION OF THE INVENTION

Figure 1:
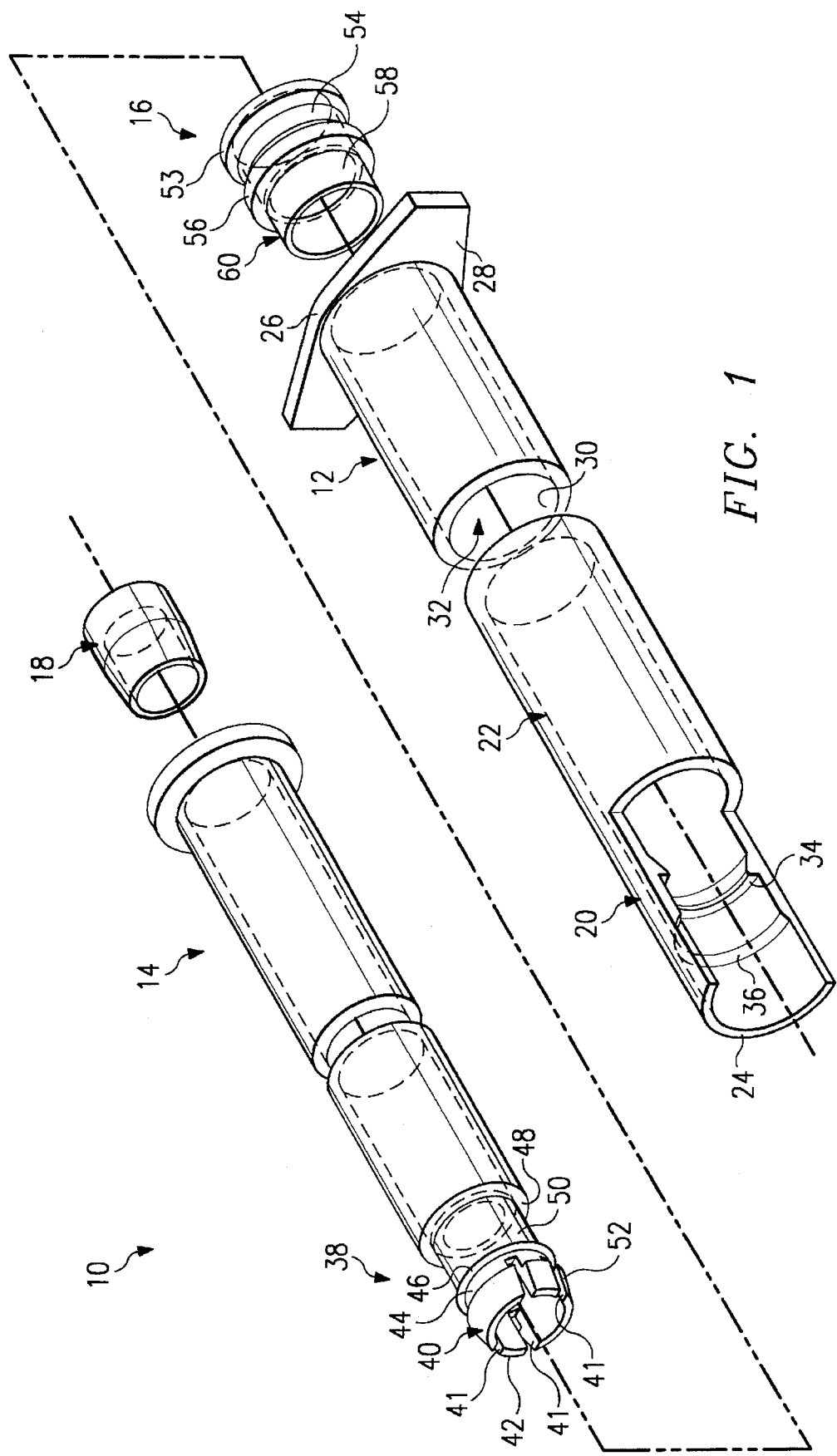
FIG. 1 is an exploded perspective view of a syringe body and movable syringe plunger equipped with the improved locking assembly and a sliding seal for the plunger head equipped with the flexible shield of the invention.

In the description that follows, like parts will be given the same reference numeral. The drawings are generally to scale except that some of the smaller features may be exaggerated for purposes of illustration.

FIG. 1 illustrates a preferred form of the components of the improved syringe plunger locking assembly and seal of the present invention. The syringe is indicated generally by the reference numeral 10. Syringe 10 includes hollow syringe body 12 cut away and shortened for illustration. The components include a lockable syringe plunger generally designated by the reference numeral 14 and a combined sliding seal and flexible shield 16 which fits on the front of plunger 14. A plug member 18 may be force fit or otherwise fixed in the open back end of plunger 14. Plug member 18 simply prevents access to the interior of plunger 14 once the components are assembled.

FIG. 1 exemplifies a retractable syringe, although the invention is applicable to a non-retractable syringe as well. As exemplified in FIG. 1, syringe body 12 has a front portion 20 and a hollow back or rear portion 22. Body 12 is elongated longitudinally between a front tip end 24 and a back end 26 which is equipped with transverse flanges 28 for the fingers. Syringe body 12 has a wall 29 with an inner surface (constituting the interior wall of the syringe body) 30 which defines, in cooperation with plunger 14, a variable chamber 32 for injection fluid in back portion 22 of the syringe body behind the front portion 20. There would of course be other components not shown in hollow front portion 20, especially an injection needle which would extend forwardly from front 24 with its back end in fluid communication with variable chamber 32. A constriction 34 is located on inner wall surface 30 of the syringe body between the front portion 20 and the back portion 22. Front portion 20 may further include a step 36 in the wall to facilitate the release of a friction ring associated with a retraction mechanism 75 which will be discussed later in connection with FIG. 5.

Plunger 14 has a tip portion 38 comprising a catch 40 just back from front end 42 and a depression 44 just behind catch 40. Spaced behind catch 40 are front and rear stops 46 and 48 with a recess 50 between them configured to receive sliding seal 16. Catch 40 has an edge 52 from which front stop 46 is spaced to define depression 44. The term "depression" is used to indicate that the area immediately behind the outer edges of the catch is below the level of the catch with a portion of the catch extending above the rest of the plunger in that area such that a pocket is created behind the catch that can trap and hold air bubbles.

Sliding seal 16 has a hollow or a circular configuration. From back to front, it has a circular sealing flange 53, a recess 54 and second circular sealing flange 56. There is a stop surface 58 at the front of the hollow interior below the front edge of sealing flange 56. An integrally formed thin flexible shield 60 extends forwardly from sealing flange 56 in the form of a ring. It can be seen that combined sliding seal and flexible shield 16 fits over the front head end of plunger 14 in the manner shown in FIGS. 2-4.

Figure 3:
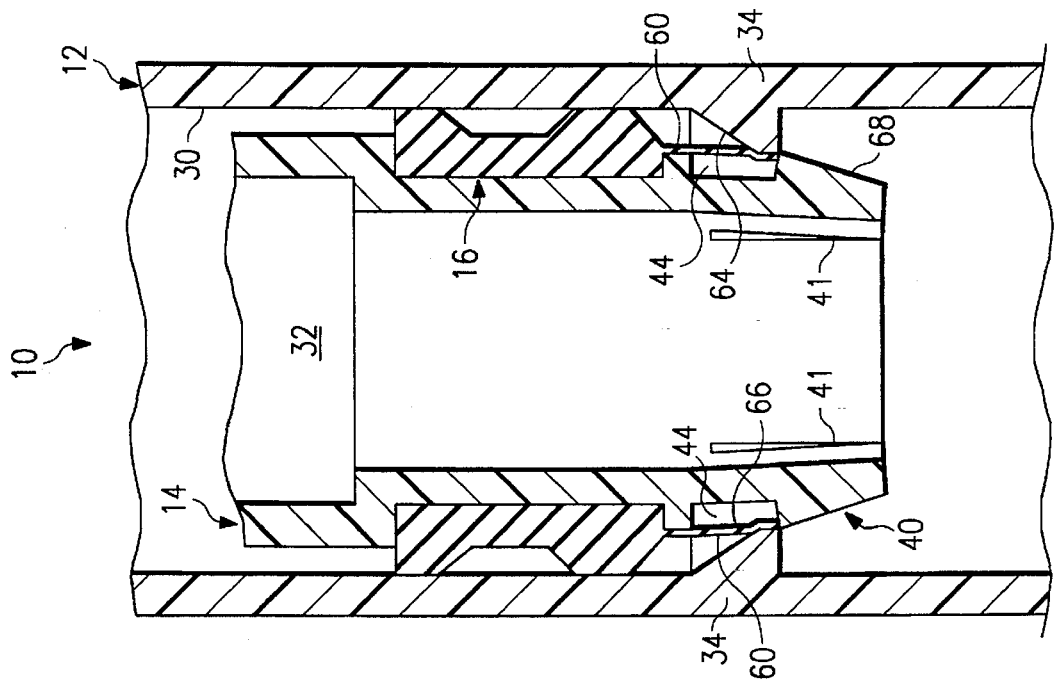
FIG. 3 is the structure of FIG. 2 upon further depression of the plunger wherein the flexible fingers carrying the catch have been flexed inwardly by the cooperating ramped surfaces just prior to locking.
Figure 2:
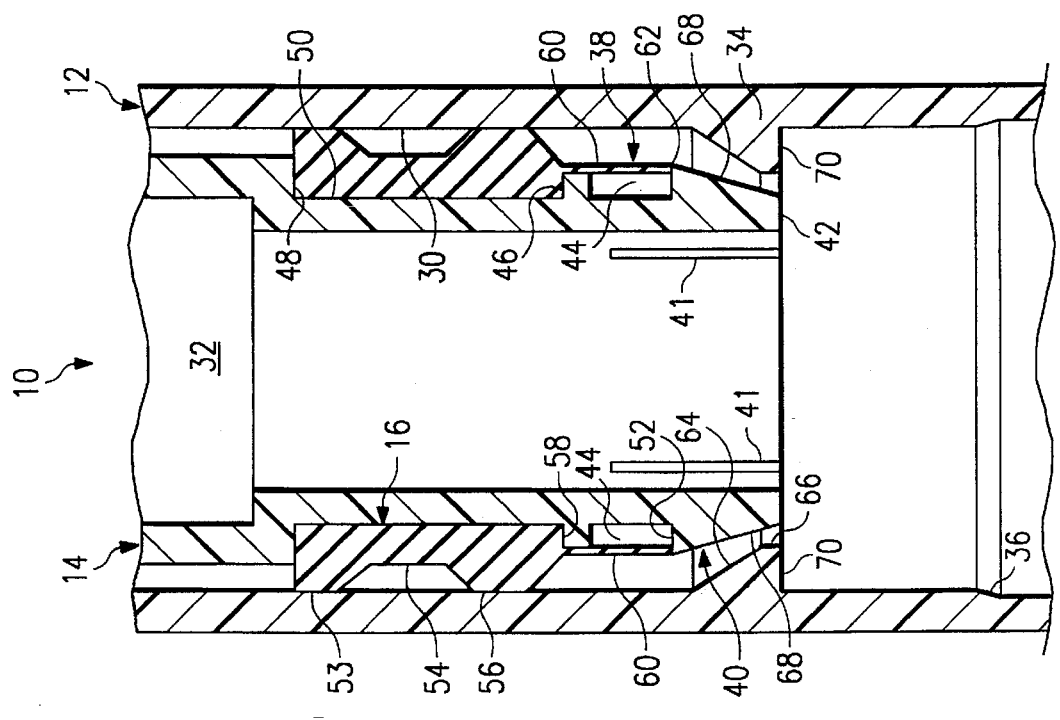
FIG. 2 is a cutaway cross sectional view showing the head of the plunger being equipped with the seal of FIG. 1, a constriction in the syringe body, a catch on the head of the plunger with a depression behind the catch covered by a flexible shield wherein the plunger is being depressed and moving toward the locking position.
Figure 4:
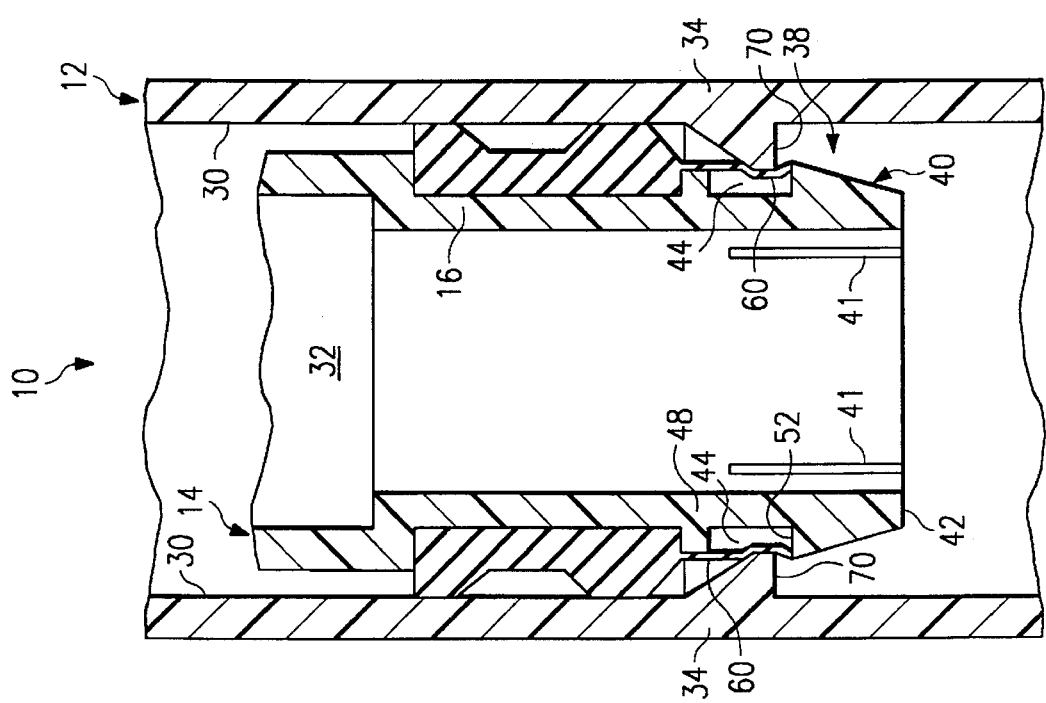
FIG. 4 shows the structure of FIG. 3 upon slight further depression of the plunger with the plunger now in the locked position with the constriction partially extending into the depression and preventing the plunger from being withdrawn.

FIGS. 2-4 isolate and enlarge the head of plunger 14, comprising the tip portion 38 back along the plunger 14 to a little past the front and rear stops 46 and 48 and the sliding seal 16, and the portion of syringe body 12 which contains constriction 34. Combined sliding seal and flexible shield 16 is installed in recess 50 with the back end of sliding seal 16 against rear stop 48 and stop surface 58 against the back of front stop 46. Flexible shield 60 is seen extending forwardly over front stop 46 spaced above depression 44 adjacent catch 40. Thus, the flexible shield is carried by the plunger head over the depression 44 behind catch 40. The forward end of flexible shield 60 is at 62.

Constriction 34 has an inwardly angled surface on ramp 64 leading to the narrowest point thereof at 66. Constriction 34 is an inwardly extending projection which cooperates with a corresponding tapered outer surface 68 of the catch on tip portion 38 of the plunger head which may be regarded as that portion forward of front stop 46. The constriction is like an annular ramp 64 on inner wall surface 30 of syringe body 12. Ramp 64 culminates in transverse surface 70 which can engage a corresponding transverse surface 52 on catch 40 when the tip portion of the plunger head is advanced to pass through constriction 34.

Figure 5:
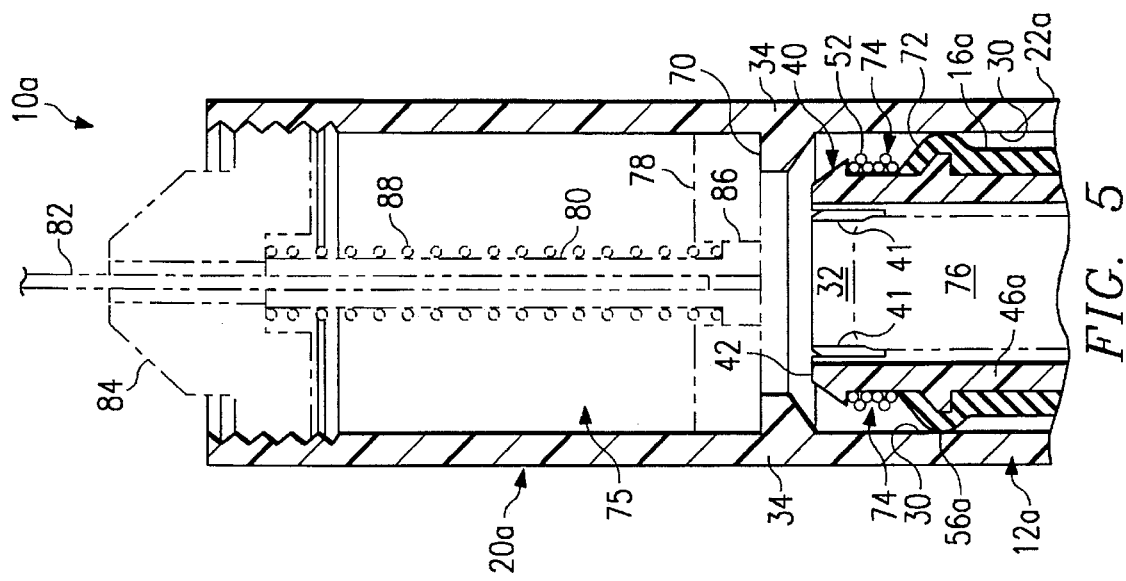
FIG. 5 is a partial cross sectional view of the front end of combined components like those of FIG. 1, with a schematically illustrated retraction mechanism in dotted outline and illustrating how bubbles of air can accumulate under the catch if a conventional sliding seal is employed.

In cross section, catch 40 looks somewhat like an arrowhead or "fishhook" as seen in FIG. 2. The tip portion 38 of the plunger head, preferably comprises a plurality of resilient fingers best seen in FIG. 1 which are separated by slots 41. Slots 41 facilitate flexing of the tip portion of the plunger head. The resilient fingers are arcuate portions extending between the slots. The resilient fingers are designed to engage annular ramp or constriction 34 in response to depression of plunger 14 at the end of an injection cycle. The front of plunger 14 of course must have something to seal it such as illustrated in FIG. 5. The exact location of the front of variable chamber 32 will depend on the specific kind of retraction mechanism that is employed with the locking assembly.

The position of plunger 14 in FIG. 2 is shown as the plunger is approaching the end of an injection cycle. It is important that flexible shield 60 guard depression 44 behind catch 40 to prevent the collection or entrapment of air bubbles behind catch 40. Flexible shield 60 may be said to be positioned between the sliding seal and the catch and over the depression at a radial distance from the center line of the syringe which is generally equal to the radial distance of the catch from the center line of the syringe. It is preferable that the outer rear edge 52 of the catch and the flexible shield come together at 62. Sliding seal 60 is spaced above the depression radially even with the outermost portion of catch 40.

FIG. 3 shows syringe 10 upon further depression of plunger 14 just before the locking assembly is engaged. The tip portion of plunger 14 is flexed inwardly as evidenced by some distortion of slots 41. The resilient fingers have been distorted inwardly by interaction between ramp surface 64 of constriction 34 and tapered outer surface 68 of catch 40 on the plunger tip. Constriction 34 preferably has a small flat area 66 at its narrowest point which contributes to strength and ease of molding. Some distortion of flexible shield 60 can be seen at its forward portion where it slides over flat 66. Flexible shield 60 is relatively thin as compared to sliding seal 16, and it is resilient. The distortion caused by shield 60 sliding over flat 66 of projection 34 does not consume any appreciable mount of energy or interfere in any way with the movement of the plunger.

FIG. 4 illustrates the position of syringe 10 after the plunger has been depressed a slight further distance from that of FIG. 3. The locking assembly is now engaged. If plunger 14 is now pulled back relative to syringe body 12, catch 40 cooperates with constriction 34 to prevent more than a minor amount of movement relative to syringe body 12. The outer edges of surfaces 52 of catch 40 and the outer edges of surface 70 of constriction 34 interfere with rearward movement of plunger 14. This occurs because in FIG. 4 the resilient leading tip portion 38 of the plunger head has flexed outwardly returning to the configuration of FIG. 2.

It will be noted that some portion of constriction 34 is received in depression 44 without any resistance from flexible shield 60 because flexible shield 60 has a thickness that is significantly less than the depth of depression 44 and there is nothing behind it to resist deformation. Alternatively, if a separate seal member is employed to fit in depression 44 instead of flexible shield 60, it needs to have an outer surface in line with the outer edge of surface 52 at the back of catch 40. Such a seal member must be of soft material which is easily compressed by the narrowest portion 66 of constriction 34 when the locking assembly is locked as shown in FIG. 4. The material from which conventional sliding seals 16 are made is considered too hard for this purpose.

FIG. 5 illustrates the problem that exists in reference to a locking assembly which utilizes some portions of the invention. In FIG. 5, parts that are similar to the invention shown in the remainder of the drawings but which may have some differences, include a letter identification along with the number. FIG. 5 represents the front portion of a similar syringe 10a which illustrates the locking mechanism of the invention with a retractable syringe of the type shown in my patent application, Ser. No. 08/125,292, now U.S. Pat. No. 5,385,551. Syringe body 12a has a front portion 20a which in dotted outline represents a retraction mechanism with features of the retraction mechanism shown in dotted outline. Constriction 34 is present and effectively separates front portion 20a from back portion 22a of syringe body 12a. The front tip end of plunger 14a is seen with a front stop 46a and conventional siding seal 16a. Spaced ahead of the forward portion 72 of sliding seal 16a a plurality of air bubbles 74 are shown trapped in a depression between portion 72 and the transverse surface 52 behind catch 40. Actually we have more often seen one large bubble trapped in that area which extends outwardly to wall surface 30. It has been found that bubbles trapped in this manner tend to adhere by surface tension and are very difficult to remove by tapping or any other means.

One might visualize moving conventional seal 16a forward so that its leading sealing flange 56a lies close behind surface 52 of catch 40. This could avoid the effective presence of what has been referred to as a depression behind the hook portion of catch 40. The depression behind surface 52 would be occupied by a portion of the flange 56a and there would be no "pocket" for bubbles to collect there. If this were done, it is not hard to visualize that the forward sealing flange 56a in such close proximity adjacent front stop 40 would strike constriction 34 when the plunger is depressed in order to lock it at the end of an injection cycle and this will prevent reliable locking of the locking assembly. The rubber sliding seal would bunch up, wrinkle and interfere with locking.

The dotted elements in FIG. 5 represent an exemplary front retraction mechanism 75 including a plug member 76 to seal the open front end of plunger 14a, a ring member 78 to frictionally hold a needle holder 80 which holds an injection needle 82 with its outer end extending through a nose piece 84 fixed at the front of front portion 20a by means of threads or other fastening means. Needle holder 80 has an enlarged head portion 86 fictionally held in ring member 78 and is biased for retraction by spring 88. Since the front end of needle holder 80 is restrained from forward movement by contact with nose piece 84, depression of the plunger as catch 40 passes through constriction 34 results in sliding ring member 78 away from head 86 until a biasing force provided by spring 88 exceeds the frictional holding force between members 78 and 86. This causes the needle holder and injection needle 82 to move into the hollow open front end of plunger 14a, dislodging plug member 76 and causing the needle holder and needle to be retracted into the plunger. Immediately following or contemporary with this sequence of retraction, cooperating surfaces behind catch 40 and the front of constriction 34 cause the plunger to be locked in the manner shown in FIGS. 2–4.

Figure 8:
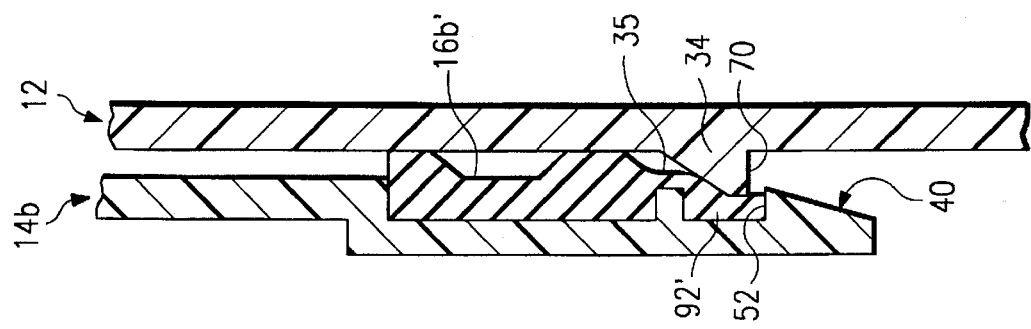
FIG. 8 shows the locking assembly of FIG. 7 with a connection between the sliding seal and the seal member.
Figure 7:
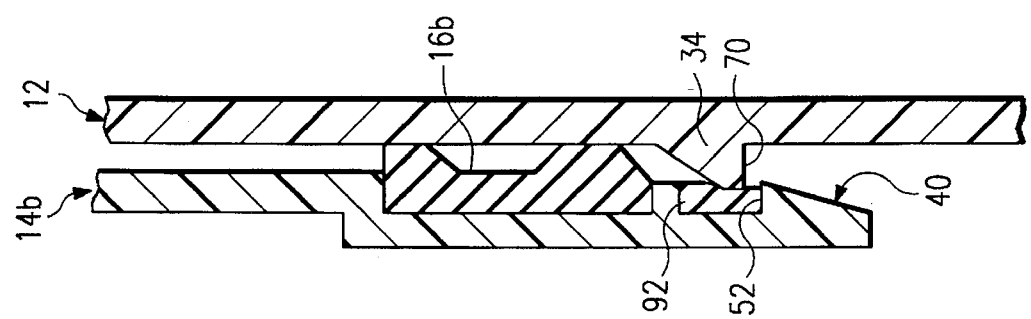
FIG. 7 shows engagement of a portion of the locking assembly of FIG. 6 wherein a portion of the constriction compresses the soft seal member and thereby exposes opposing locking surfaces on the catch and constriction.
Figure 6:
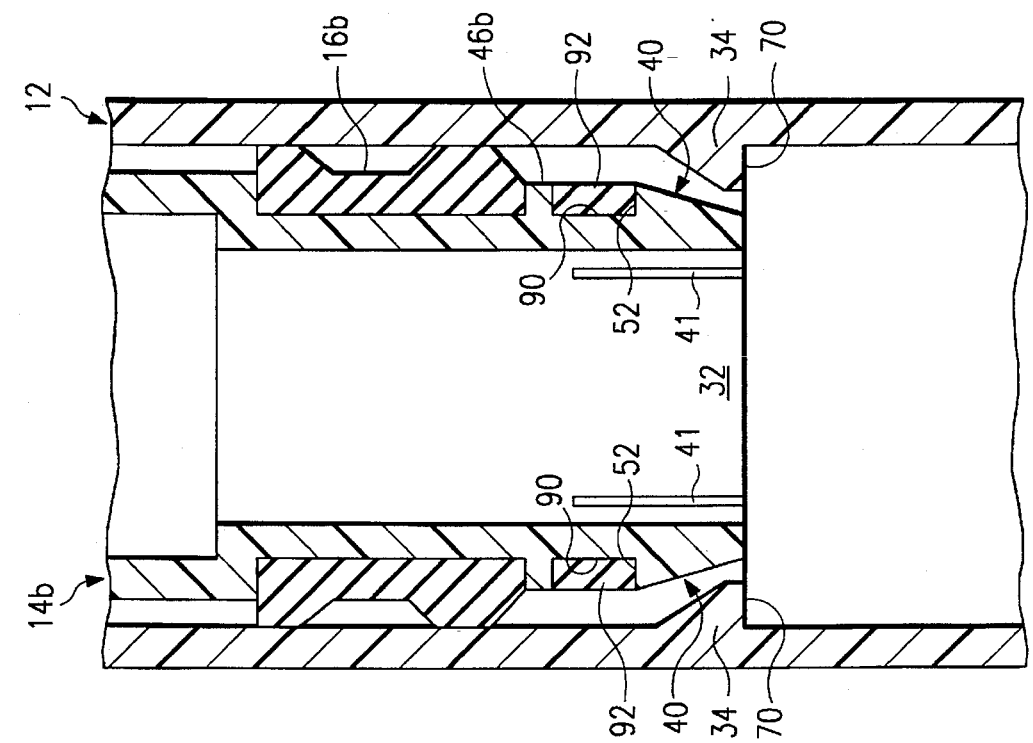
FIG. 6 represents an alternative embodiment wherein a pocket behind the catch of the tip of the plunger is occupied by a soft resilient seal member which is separate from the main sliding seal of the plunger.

FIGS. 6 and 7 illustrate how a "pocket" 90 behind catch 40 can be prevented from trapping air bubbles by the presence of a seal member 92 which is separate from a modified sliding seal 16b on a modified plunger 14b of syringe 12. FIG. 6 is equivalent to the position shown in FIG. 2 and FIG. 7 is equivalent to the position shown in FIG. 4 with only a cross-sectional view of a part of the structure shown on the right side of FIG. 6. FIG. 8 is just like FIG. 7 except that modified sliding seal 16b' is connected to modified seal member 92' by a bridging portion 35.

In FIG. 6 front stop 46b on plunger 14b is made even in diameter with the outermost portion of catch 40 creating a pocket 90 immediately behind surface 52. Otherwise plunger 14b is the same as plunger 14. Seal member 90 is preferably a band or ring member which circumscribes the tip portion of plunger 14b and is received in pocket 90, which may also be referred to as a depression. Like depression 44 it presents a space behind catch 40 where air bubbles can undesirably collect. By making front stop 46b even with the outer edges of catch 40, seal member 92 may be of rectangular cross section for ease of fabrication.

When plunger 14b is depressed it moves from the position of FIG. 6 to the position of FIG. 7 in the same manner as described in FIGS. 2-4. Because the outer diameter of the catch is bigger than the narrowest part of constriction 34, some inward flexing of the plunger tip is desirable and the tip portion snaps back to its former position. A portion of constriction 34 easily compresses seal member 92 because it is selected from soft resilient materials such as soft elastomer or a soft silicone rubber or the like or even a springy plastic foam. When seal member 92 is compressed this way the opposite locking surfaces 52, 70 are exposed and the plunger is locked in the syringe body and cannot be withdrawn.

The locking assembly of the invention can be used in a non-retractable syringe where the constriction 34 is close to the front of the syringe body and the same plunger configuration is used. In such case the plunger would have a seal at its front end. It would be helpful if the seal at the front end of the plunger had some flexibility so that the catch on the front of the plunger can move laterally as it passes through the constriction.

I claim:

1. In a syringe having a hollow syringe body elongated longitudinally between a front tip end and a back end, raid syringe body having an inner wall surface, a front portion and a hollow back portion, an exposed injection needle in fluid communication with the hollow back portion of the syringe body, a movable plunger having a head end disposed within the hollow syringe body and a sliding seal mounted on the plunger head in sliding contact with the inner wall surface to define a variable chamber for injection fluid in the back portion of the syringe body behind the front portion thereof whereby injection fluid may be passed through the needle upon movement of the plunger, wherein the improvement is a syringe having an improved locking assembly comprising:

a constriction being located on the inner wall surface of the syringe body;

the head of the plunger having a catch adapted to cooperate with said constriction to hook the plunger when the plunger is depressed to complete an injection and thereby lock the plunger in the syringe body, said catch comprising a plurality of resilient fingers which serve to engage said constriction in response to depression of the plunger at the end of an injection cycle; and a flexible shield adjacent the catch on the plunger head to prevent trapping bubbles under the catch during movement of the plunger while the syringe is being filled with injection fluid and readied for use.

2. The improved combination of claim 1 wherein the plunger head has a leading tip portion which carries the catch, with ability to flex resiliently in order to aid in hooking the plunger.

3. The improved combination of claim 2 wherein the plunger head has a depression formed behind the catch usable to receive some portion of the constriction when the plunger is depressed to cause the plunger to lock;

said flexible shield being carried by the plunger head over the depression behind the catch.

4. The improved combination of claim 3 wherein said tip portion of the plunger head has a tapered outer surface, and wherein said constriction has an inwardly angled surface leading to the narrowest point thereof which cooperates with said corresponding tapered outer surface on the tip portion of the plunger head to facilitate flexing of the tip portion as it passes through the constriction to lock the plunger.

5. The improved combination of claim 4 wherein the constriction is formed as an annular ramp on the inner wall surface of the syringe body, said ramp culminating in an edge which engages said catch on the plunger head as soon as the catch passes through the constriction in response to outward flexing of the tip portion of the plunger head.

6. The improved combination of claim 5 wherein the sliding seal in sliding contact with the inner wall surface is spaced apart from said catch behind the depression;

said flexible shield being positioned between the sliding seal and the catch and over the depression at a radial distance from the center of the syringe generally equal to the radial distance of the catch.

7. The improved combination of claim 6 wherein said flexible shield constitutes a forward extension integral with the sliding seal and spaced above the depression radially even with the outermost part of the catch.

8. The improved combination of claim 7 wherein the head of the plunger has longitudinally spaced apart front and back stops, the sliding seal is sized to fit in the space between the said stops to hold it in place when the plunger is moved, said depression is formed between the front stop and the catch and said for, yard extension of the sliding seal passes over the front stop and the depression to reach the catch.

9. In a retractable syringe of the type having a hollow elongated syringe body with an interior wall and with a hollow front portion containing a retractable injection needle and at least pan of a retraction assembly and a movable plunger having a head, which is a leading had, and a sliding seal on the head which sealingly slides alone the interior wall of the syringe body thereby forming a variable chamber for injection fluid behind the hollow front portion of the syringe body wherein the variable chamber is in fluid communication with the injection needle so that injection fluid can be drawn into and expelled from the variable chamber by longitudinal movement of the plunger relative to the syringe body, wherein the improvement is a syringe having an improved locking assembly comprising:

the syringe body having a constriction between the variable chamber and the hollow front portion of the syringe body;

the head of the plunger having a leading tip portion configured to pass in close proximity with the constriction, when the plunger is depressed at the end of an injection cycle, which cooperates with the constriction to hook said leading tip portion an that the depressed plunger cannot be withdrawn from the syringe body;

a depression located on the plunger behind the leading tip portion of the head of the plunger and located distally of said sliding seal; and a seal member positioned over said depression on the head of the plunger to inhibit and prevent air bubbles from lodging behind said leading tip portion when the syringe is filled with fluid and readied for use.

10. The improved combination of claim 9 wherein said leading tip portion carries a earth and has the ability to flex resiliently in order to aid in hooking the plunger.

11. The improved combination of claim 10 wherein said constriction is formed as an annular ramp on the interior wall of the syringe body culminating in an edge which engages a cooperating edge on said catch.

12. The improved combination of claim 11 wherein said seal member is positioned between the sliding seal on the head of the plunger and the catch above said depression at a radial distance from the center of the syringe generally equal to the outer edge of the fitch in order to prevent tripped air bubbles from lodging behind said catch.

13. The improved combination of claim 9 wherein said leading tip portion comprises a plurality of resilient fingers at least some of which carry a catch which cooperates with said constriction to lock the plunger head inside the syringe body.

14. In a syringe having a forward portion, an internal wall which comprises a chamber for fluid and a plunger having a front end with a sliding seal member in movable sealing contact with the internal wall to draw fluid into said chamber and expel said fluid through a needle in the forward portion of the syringe, wherein the improvement is a syringe having an improved seal and locking assembly comprising:

the forward portion of the syringe having an entrance to said chamber and an inwardly extending projection from said internal wall proximate to the entrance of the chamber;

the front end of the plunger having a fitch adapted to engage the inwardly extending projection as the last of the fluid is expelled from the chamber upon forward movement of the plunger relative to the syringe;

the sliding seal member is mounted on the front end of the plunger in sliding sealing contact with the internal wall of the syringe, said sliding seal member being spaced behind said catch; and a seal member mounted around the plunger between the sliding seal member and catch, sized to inhibit and prevent air bubbles from lodging behind the catch when the syringe is filled with fluid, without interfering with operation of the catch.

15. The improved combination of claim 14 wherein the front end of the plunger has a pocket formed behind the catch usable to receive some portion of the inwardly extending projection when the plunger is depressed thereby causing the plunger to lock;

said seal member being carried by the plunger head behind the catch, said seal member being configured to occupy said pocket in order to prevent trapping of bubbles behind the catch.

16. The improved combination of claim 15 wherein said seal member is configured to fit in the pocket behind the catch in such a manner that its outer diameter is even with the outer diameter of the catch.

17. The improved combination of claim 16 wherein said seal member is connected to said sliding seal member.

18. The improved combination of claim 15 wherein the catch on the front end of the plunger comprises a plurality of resilient fingers upon which said catch is carried which enable the catch to move laterally as it passes by the inwardly extending projection and locks.

19. In a syringe having a hollow syringe body elongated longitudinally between a front tip end and a back end, said syringe body having an inner wall surface, a front portion and a hollow back portion, an exposed injection needle in fluid communication with the hollow back portion of the syringe body, a movable plunger having a head end disposed within the hollow syringe body and a sliding seal mounted on the plunger head in sliding contact with the inner wall surface to define a variable chamber for injection fluid in the back portion of the syringe body behind the front portion thereof whereby injection fluid in the back portion of the needle upon movement of the plunger, wherein the improvement is a syringe having an improved locking assembly comprising:

a constriction being located on the inner wall surface of the syringe body, said constriction having an inwardly angle surface leading to the narrowest point thereof;

the head of the plunger having a catch adapted to cooperate with said constriction to hook the plunger when the plunger is depressed to complete an injection and thereby lock the plunger in the syringe body;

the head of the plunger having a leading tip portion which caries the catch, with ability to flex resiliently in older to aid in hooking the plunger, said leading tip portion having a tapered outer surface which cooperates with said corresponding inwardly angled surface of said constriction to facilitate flexing of the tip portion as it passes through the constriction to lock the plunger;

the head of the plunger having a depression formed behind the catch and located distally of said sliding seal, said depression being usable to receive some portion of the constriction when the plunger is depressed to cause the plunger to lock; and a flexible shield being carried by the plunger head over the depression behind and adjacent the catch to prevent trapping bubbles under the catch during movement of the plunger while the syringe is being filled with injection fluid and readied for use.

20. The improved combination of claim 19 wherein the constriction is formed as an annular ramp on the inner wall surface of the syringe body, said ramp culminating in an edge which engages said catch on the plunger head as soon as the catch passes through the constriction in response to outward flexing of the tip portion of the plunger.

21. In a retractable syringe of the type having a hollow elongated syringe body with an interior wall and with a hollow front portion containing a retractable injection needle and at least pan of a retraction assembly and a movable plunger having a head, which is a leading head, and a sliding seal on the head which sealingly slides along the interior wail of the syringe body thereby forming a variable chamber for injection fluid behind the hollow front portion of the syringe body wherein the variable chamber is in fluid communication with the injection needle so that injection fluid can be drawn into and expelled from the variable chamber by longitudinal movement of the plunger relative to the syringe body, wherein the improvement is a syringe having an improved locking assembly comprising;

the syringe body having a constriction between the variable chamber and the hollow front portion of the syringe body, said constriction formed as an annular ramp on the interior wall of the syringe body culminating in an edge;

the head of the plunger having a leading tip portion on configured to pass in close proximity with the constriction, when the plunger is depressed at the end of an injection, cycle which cooperates with the constriction to hook said leading tip portion so that the depressed plunger cannot be withdrawn from the syringe body, said leading tip portion carrying a catch with an edge which cooperatively engages said edge on said ramp, said leading tip portion further having the ability to flex resiliently in order to aid in hooking the plunger;

a depression on the plunger behind the leading tip portion of the head of the plunger and located distally of said sliding seal; and a seal member positioned around said depression on the head of the plunger to inhibit and prevent air bubbles from lodging behind said leading tip portion when the syringe is filled with fluid and readied for use.

* * * * *

UNITED STATES PATENT AND TRADEMARK OFFICE
CERTIFICATE OF CORRECTION

PATENT NO. : 5,637,092
DATED : June 10, 1997
INVENTOR(S) : Thomas J. Shaw

It is certified that error appears in the above-indentified patent and that said Letters Patent is hereby corrected as shown below:

```
Column 8, line 5, replace "raid: with --said--;
Column 9, line 4, replace "for yard" with --forward--;
Column 9, line 9, replace "pan" with --part--;
Column 9, line 10, replace "had" with --head--;
Column 9, line 11, replace "alone" with --along--;
Column 9, line 27, replace "an" with --so--;
Column 9, line 38, replace "earth" with --catch--;
Column 9, line 48, replace "fitch" with --catch--;
Column 9, line 48, replace "tripped" with --trapped--;
Column 9, line 66, replace "fitch" with --catch--;
Column 10, line 42, replace "in the back portion of" with--
    may be passed through--;
Column 10, line 54, replace "caries" with --carries--;
Column 10, line 54, replace "older" with --order--;
Column 11, line 9, replace "Plunger." with --plunger head.--;
Column 11, line 13, replace "pan" with --part--;
Column 11, line 16, replace "wail" with --wall--; and
Column 12, line 4, delete "on".
```

Signed and Sealed this

Third Day of March, 1998

Attest:

BRUCE LEHMAN

Attesting Officer

Commissioner of Patents and Trademarks